United States Patent [19]

DuBois

[11] 4,454,290

[45] Jun. 12, 1984

[54] STEVIOSIDE ANALOGS

[75] Inventor: Grant E. DuBois, Palo Alto, Calif.

[73] Assignee: Dynapol, Palo Alto, Calif.

[21] Appl. No.: 272,798

[22] Filed: Jun. 11, 1981

Related U.S. Application Data

[63] Continuation-in-part of Ser. No. 189,243, Sep. 22, 1980, Pat. No. 4,332,830.

[51] Int. Cl.³ .............................................. C07H 15/24
[52] U.S. Cl. ..................... 536/18.1; 424/48; 424/49; 426/3; 426/548; 426/552; 426/573; 426/576; 426/590; 426/658
[58] Field of Search ................ 536/4, 18.1; 260/503.5; 560/6; 426/548, 658

[56] References Cited

U.S. PATENT DOCUMENTS

| | | | |
|---|---|---|---|
| 1,984,714 | 12/1934 | Weiland et al. | 260/503.5 |
| 2,107,508 | 2/1938 | Rummelsburg | 260/503.5 |
| 3,723,410 | 3/1973 | Persinos | 536/4 |
| 3,732,202 | 5/1973 | Jewers et al. | 536/18.1 |
| 4,082,858 | 4/1978 | Morita et al. | 536/4 |
| 4,226,804 | 10/1980 | DuBois et al. | 260/501.11 |

OTHER PUBLICATIONS

Wood, Jr. et al., "Chem. Abst.", vol. 50, 1956, p. 5581(d).

Mosettig et al., "Jour. Amer. Chem. Soc.", vol. 85, pp. 2305-2309, 1963.
Sakamoto et al., "Chem. Abst.", vol. 84, 1976, P101729(j).
Kohda et al., "Chem. Abst.", vol. 85, 1976, P193026(z).

*Primary Examiner*—Johnnie R. Brown
*Attorney, Agent, or Firm*—Burns, Doane, Swecker & Mathis

[57] ABSTRACT

Analogs of the glycoside stevioside are disclosed. These materials have the formula

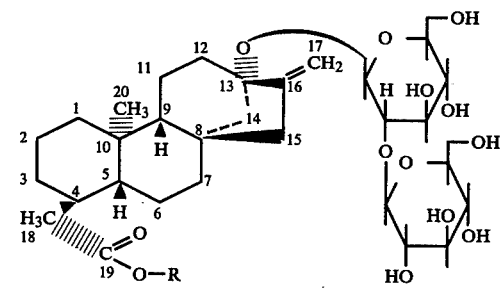

wherein R is a simple physiologically acceptable non-carbohydrate polar organic group. The analogs are sweet and find use as sweeteners.

13 Claims, No Drawings

STEVIOSIDE ANALOGS

REFERENCE TO RELATED APPLICATION

This is a continuation-in-part of U.S. patent application Ser. No. 189,243, filed on Sept. 22, 1980, now U.S. Pat. No. 4,332,830.

BACKGROUND OF THE INVENTION

1. Field of the Invention

This invention relates to chemical analogs of the sweet glycoside, stevioside, which are themselves sweet and useful as sweeteners and which do not degrade under conditions of use to form physiologically undesirable steviol as does stevioside.

2. The Prior Art

The leaves of the Paraguayan shrub *Stevia rebaudiana* Bertoni have long been known to be sweet. A sweet crystalline glycoside has been isolated from these leaves. This compound, named stevioside by the Union International de Chimie in 1921, has been reported to be about 300 times as sweet as sucrose by Bridel et al., *Compt. Rend.*, 192, 1123-5 (1931) and *J. Pharm. Chim.*, 14(3), 99-113; 14 (4), 154-161 (1931). Mosettig et al. reported the absolute configuration of stevioside as shown in general formula I.

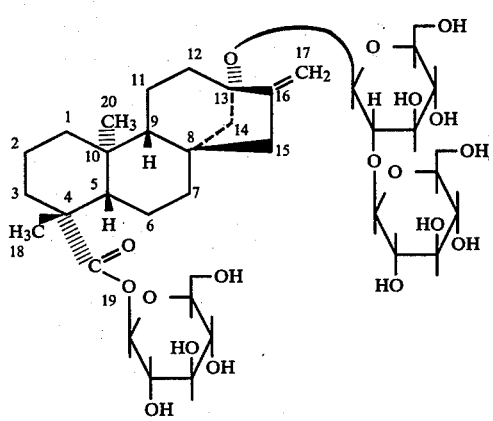

in *J. Am. Chem. Soc.*, 85, 2305-2309 (1963). This material has attracted substantial interest as a potential sweetener, particularly in the orient where its plant source is now cultivated and where crude stevioside-containing extracts are used as sweeteners. (see Japanese Patent Nos. 51-52200; 52-47956, 7 and 9; 52-51069; 52-57198 and 9 and 52-62300.)

Stevioside's acceptance in the United States has been slow. Possibly, this is because its sweet taste is contaminated by a substantial degree of bitterness. (Bridel et al., above). It also may be due to concerns about the compound's safety.

In 1966, P. V. Vignais and coworkers reported the results of a study concerned with elucidation of the mode of action of the respiratory toxin, atractyligenin. Included in their study were several compounds of related structure including steviol (II), the aglycone of stevioside.

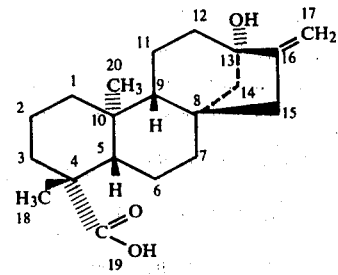

Surprisingly, in cell mitochrondria, steviol was found to be an even more potent inhibitor of ATP synthetase then atractyligenin. (*Biochim. Biophys. Acta*, 118, 465-483 (1966).) In addition, steviol is reported to exhibit antiandrogenic effects (Dorfman, R. I., et al., *Endocrinology*, 67, 282-285 (1965).) Clearly, if stevioside was converted to steviol in vivo, significant toxicity may be expected. Recent results suggest the likelihood that stevioside would be largely converted to steviol in vivo, and further that the steviol thus produced would subsequently be completely absorbed through the gastrointestinal tract wall. (R. Wingard, J. Dale, J. Brown, R. Hale, F. Enderlin, C. Seitz, *Experientia*, 36, 519(1980).) Thus, as a result of a combination of the Vignais and Wingard work, it may be concluded that, with widespread use, stevioside may be expected to exhibit significant acute toxicity. If, however, stevioside's metabolism to steviol could be prevented, that is if a potently sweet analog could be developed which was not degraded to steviol, safety for use in foods would be anticipated.

STATEMENT OF THE INVENTION

A family of new chemical analogs of stevioside has now been discovered. These materials are useful as sweeteners and unexpectedly have the property of being stable to mammalian gastrointestinal tract conditions and not generating steviol in vivo. These compounds have the chemical structures of formula III,

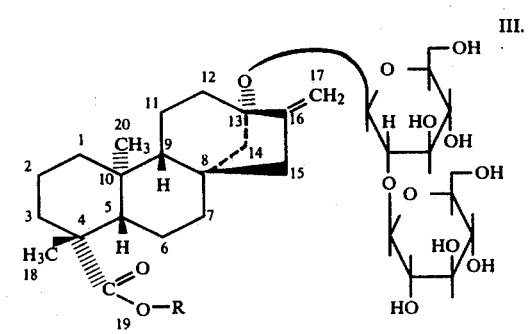

wherein R is a simple noncarbohydrate polar group. These compounds may be further classified as non-glycosidic polar esters of steviolbioside.

In another aspect, this invention involves the use of these new compounds as sweeteners for comestibles wherein they are admixed with said comestibles.

In yet another aspect, this invention concerns a method for preparing these new compounds and their intermediates.

DETAILED DESCRIPTION OF THE INVENTION

The Compounds

In this Description of the Invention reference will be made to a variety of related diterpenoid compounds. These compounds include:

Stevioside—the natural product shown in general formula I

Steviol—the aglycone of stevioside shown in general formula II

Steviolbioside—the base hydrolysis product of stevioside having the structure shown in general formula IV

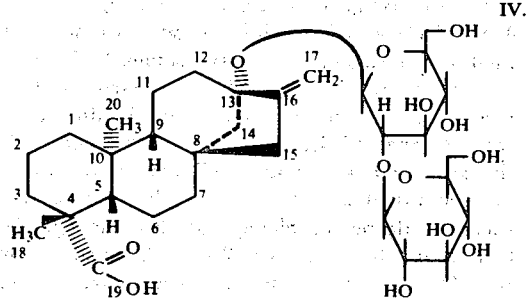

Steviolbioside esters—the compounds having the structure shown in general formula III wherein "R" is as defined The compounds of this invention differ structurally from art-known stevioside and steviolbioside in the nature of the "R" substituent attached to the C-19 oxygen. In the present material, R is a physiologically acceptable noncarbohydrate polar organic group. R should not have oxygen substituted on its α-carbon, that is, it should be α-carbon oxygen free as such substitution in this position is equivalent to acetal functionality which is unstable in vivo and could lead to "R-group" cleavage and formation of steviol. The α-carbon can be substituted with carboxyl, sulfo, phospho, and similar polar groups, however.

R may preferably be selected from among 1 to 10 carbon atom polar organic groups. Preferably, R has from 2 to about 5 carbon atoms. Of necessity, these polar groups will include atoms beyond carbon and hydrogen such as the heteroatoms oxygen, sulfur, nitrogen and phosphorous. These heteroatoms may form anionic or cationic or zwitterionic polar moieties including sulfonate, sulfamate, carboxylate, and phosphonate anions, ammonium cations and combinations thereof. These polar moieties are accompanied by physiologically acceptable counterions. Representative R groups include the materials listed in Table I. Table I also lists precursors or precursor sequences which can be used to insert these R groups as will be set forth herein as Preparative Methods.

TABLE I

| R GROUP | Precursors |
|---|---|
| 1-5 carbon alkyl terminal sulfonates.<br>—(CH$_2$)$_n$—SO$_3^-$M$^+$*<br>n = 1-5, preferably 2-5, more preferably 3 or 4 and most preferably 3 | Br—(CH$_2$)$_n$—SO$_3^-$M$^+$<br>1,3-Propane sultone<br>1,4-Butane sultone |
| 1-5 carbon alkyl polysulfonates (preferably 2-5 carbons)<br>—CH$_2$—CH—(SO$_3^-$M$^+$)$_2$<br>—(CH$_2$)$_2$—CH—(SO$_3^-$M$^+$)$_2$<br>—CH$_2$—CH(SO$_3^-$M$^+$)—CH$_2$—SO$_3^-$M$^+$ | Br—(CH$_2$)$_2$—CH(SO$_3^-$M$^+$)$_2$<br><br>(structure with (CH$_2$)$_n$ bridging two SO$_2$ groups bonded to O, and phenol OH), n = 1,2<br>Etc. |
| 1-5 carbon alkyl terminal carboxylates<br>—(CH$_2$)$_n$—COO$^-$M$^+$<br>n = 1-5 preferably 1-3 | Br—(CH$_2$)$_n$—COOGp* |
| 1-5 carbon alkyl polycarboxylates<br>—CH$_2$—COO$^-$M$^+$—(CH$_2$)$_2$—COO$^-$M$^+$<br>Etc. | Br—CH$_2$—COOGp—(CH$_2$)$_2$—COOGp |
| 1-5 carbon alkyl terminal phosphonates<br>—(CH$_2$)$_n$—PO$_3$H$^-$M$^+$<br>n = 1-5, preferably 2-4 | Br—(CH$_2$)$_n$—PO$_3$(Gp)$_2$ |
| 1-5 carbon polyhydroxyls<br>(CH$_2$)$_n$ —CH(OH)—CH(OH)—CH$_2$OH<br>(CH$_2$)$_n$ —CH(OH)—CH$_2$OH<br>Etc. n = 1,2 | Br—(CH$_2$)$_n$—CH(epoxide)CH$_2$ →<br><br>—(CH$_2$)$_n$—CH(epoxide)CH$_2$ $\xrightarrow{H_3O^+/THF}$<br><br>—(CH$_2$)$_n$—CH(OH)—CH$_2$OH<br>or |

TABLE I-continued

| R GROUP | Precursors |
|---|---|
| | 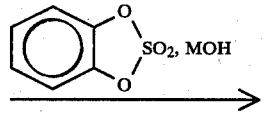 |
| 1-5 carbon primary amine salts<br>—$(CH_2)_n$—$NH_3^+X^-$*<br>n = 1-5, preferably 2-4 | Br—$(CH_2)_n$—Br →<br>—$(CH_2)_n$—Br →<br>—$(CH_2)_n$—$N_3$ $\xrightarrow[\text{MEOH}]{\text{NaBH}_4 / \text{NiCl}_2.6H_2O}$<br>—$(CH_2)_n$—$NH_3^+Cl^-$ |
| 1-5 carbon alkyl sulfamates<br>—$(CH_2)_n$—NH—$SO_3^-M^+$<br>n = 1-5, preferably 2-4 | —$(CH_2)_n$—$NH_3^+Cl^-$ $Et_3N/DMF$,<br>[benzene-fused cyclic sulfite] $SO_2$, MOH →<br>—$(CH_2)_n$—$NHSO_3^-M^+$<br>(DuBois and Stephenson, J. Org. Chem. 1980, 45, 5371-3.) |
| 1-5 carbon alkyl amino-carboxylates<br>—$(CH_2)_n$—$CH(NH_3^+)$—$COO^-$<br>n = 1-4, preferably 2-3 | Br—$(CH_2)_n$—$CH(NHCOOCH_2Ph)COOGp$ |
| —$(CH_2)_n$—$CH(COO^-)$—$(CH_2)_m$—$NH_3^+$<br>n = 1-2, m = 1-3 | Br—$(CH_2)_m$—$CHBrCOOGp$ →<br>—$CH(COOGp)$—$(CH_2)_m$—Br $\xrightarrow{\text{NaN}_3}{\text{DMF}}$<br>—$CH(COOGp)$—$(CH_2)_m$—$N_3$ $\xrightarrow{\text{KOH}}$<br>—$CH(COO^-K^+)$—$(CH_2)_m$—$N_3$—<br>$\xrightarrow{\text{NaBH}_4, \text{NiCl}_2.6H_2O \text{ MeOH}}$<br>—$CH(COO^-)$—$(CH_2)_m$—$NH_3^+$ |

*$M^+$ = physiologically acceptable alkali metal cation, or alkaline earth metal particularly $Na^+$, $K^+$, $Mg^{++}$ or $Ca^{++}$
*$X^-$ = physiologically acceptable anion such as $Cl^-$
*Gp = protecting group, e.g. —$CH_3$, or —$C_2H_5$, or the like that protects a labile functionality and is thereafter removed.

These R groups are merely representative. For example, straight chain ester substituents have been shown but branched materials can be used as well. Other equivalent organic groups may be substituted so long as they are noncarbohydrate and polar.

Among the compounds of this invention preference is given those having 1-5 carbon alkyl terminal sulfonate R groups while among these, the compounds wherein R is —$(CH_2)_3$—$SO_3^-K^+$ or —$(CH_2)_3$—$SO_3^-Na^+$ are more preferred. These two most preferred compounds can be named as steviolbioside, sulfopropyl ester, potassium and sodium salts.

Preparative Methods

The compounds of the invention can be prepared from commercially available stevioside by the general preparative scheme of saponifying stevioside to produce steviolbioside and then reacting steviolbioside with an "R-addition" reagent, that is a reagent that will add the desired R to the steviolbioside in place of the hydrogen atom of steviolbioside's C-19 oxygen atom.

More particularly, the saponification is carried out by reacting stevioside with a molar excess (at least 5 equivalents) of a strong base, especially aqueous or alkanolic or mixed aqueous-alkanolic KOH or NaOH and particularly aqueous and/or methanolic KOH, at elevated temperatures such as from 50° C. to 150° C., preferably 60°-100° C. for a time adequate to affect essentially complete saponification. An especially preferred reaction uses 40-80% methanol as a cosolvent as this gives an easily filtrable granular product. At atmospheric pressure this reaction is best carried out at about 65° C., the boiling point of methanol. The concentration of the base is generally from about 1%wt. to about 20%wt. The time required would be in the range of from 0.1 hours to 3 hours and would depend upon the temperature employed. At higher temperatures, say 100°-150° C., times from 0.1 to 1 hour are preferred. At lower temperatures, say 50°-100° C., times from 1 to 3 hours are preferred.

Following saponification, the reaction medium is generally neutralized, such as with mineral acid, and the steviolbioside is recovered. This recovery can be effected by crystallization, brought about by cooling or removal of solvent. The steviolbioside can be purified by recrystallization, column chromatography or a like process at this point. Such a purification is generally performed.

The steviolbioside (preferably recovered and purified) is contacted with the "R-addition" agent, under mildly basic conditions to effect addition. The particular "R-addition" agent employed of course depends upon the "R" group sought to be added. A list of exemplary R-addition agents is provided in Table I. In general, any reagent that will displace the steviolbioside carbonyl groups hydrogen with R, can be used. About 1 equivalent of R-addition agent is used per equivalent of steviolbioside (preferably 0.9 to 1.1 equivalents). A weak inorganic base, such as an alkali metal or alkaline earth metal carbonate, corresponding to the counterion of the final product (if any), is present in an amount about equal to the equivalents of R-addition agent. This reaction is conducted at a low to moderate temperature (0° C. to 30° C., preferably 10°–25° C.) for an extended period such as from 4 to 48 hours especially 12 to 48 hours. This reaction is carried out in liquid phase in an aprotic reaction medium, such as dimethylformamide, N-methylpyrrolidone, acetone, dimethyl sulfoxide and the like.

Following reaction with the R-addition agent and neutralization with acid, the product is recovered such as by evaporation, followed by recrystallization. Other equivalent recovery and purification processes may be employed.

These preparative conditions are merely representative. Other equivalent routes may be employed if desired.

Stability of Compounds

An important property of these stevioside analogs is their stability and resistance to conversion to steviol at the conditions of the mammalian gastrointestinal tract. This property is demonstrated in vitro by anaerobically incubating the compounds of the invention with fresh rat cecal contents of three days at 37° C. as detailed in Example 1. At these conditions, no degradation to steviol occurs to a limit of detection of 0.13%. In direct contrast, as reported in the *Experientia* paper of Wingard, et al., noted above, stevioside itself undergoes essentially quantitative degradation to steviol.

Use of the Compounds

The compounds of this invention are useful as sweeteners for comestibles. In this application, they are simply admixed with the comestible by art-known means in dry form or as solutions, preferably in water. They are, advantageously, soluble in water at usual use levels. Representative comestibles include beverages such as sodas, coffee, lemonade, wine and the like; edibles such as gelatin desserts, candy, gum, cakes, cereals and the like, personal products such as mouth wash and toothpaste as well as pharmaceuticals such as cough syrups, and flavored pills.

The compounds of this invention are about 125 to 300 times as sweet as sucrose on a weight basis. Accordingly, the amounts to be employed may be determined by fastoring usual sucrose use levels by this 125–300 value. Thus, for example, a soft drink might be sweetened by adding 0.03 to 0.15% by weight of the present compounds. Mixtures of these materials alone or with known other sweeteners (sucrose, saccharin or the like) may also be advantageously employed.

The invention will be further described by the following Examples. These are provided solely to illustrate the invention and are not to be construed as limiting its scope.

EXAMPLE I

Preparation of steviolbioside, 3-sulfopropyl ester, potassium salt

A. Steviolbioside

According to the procedure of H. B. Wood, R. Allerton, H. W. Diehl, and H. G. Fletcher (J. Org. Chem. 20, 875–883 (1955)), 771 mg (0.96 mmole) of stevioside was saponified with 25 mls 10% KOH at reflux for 1 hour. After cooling, the reaction mixture was acidified to pH 3 with 10% $H_2SO_4$. After further ice-bath cooling for several hours, filtration yielded a white solid. Recrystallization from methanol yielded 560 mg (91%) of steviolbioside as a white flocculent solid.

B. Steviolbioside, 3-sulfopropyl ester, potassium salt

A mixture of 100 mg (0.156 mmole) steviolbioside, 21 mg (0.172 mmol) 1,3-propane sultone, 24 mg (0.172 mmole) potassium carbonate, and 0.50 ml DMF was stirred vigorously at ambient temperature under an inert atmosphere for 24 hours. TLC analysis (Silica Gel F-254; $CHCl_3$—MeOH—$H_2O$/15-10-2) showed one product (Rf=0.40) and the absence of starting material. The reaction mixture was diluted with 2 ml $H_2O$, acidified with 5% HCl to pH 3 and concentrated to dryness in vacuo. The residue was recrystallized from absolute MeOH to yield 71 mg (57%) of the title compound as a white flocculent solid; mp 204°–6°; IR$\lambda_{max}^{KBr}$ 2.91 (O—H), 5.81 (C=O), 6.02 (C=$CH_2$), 8.5 (S=O), 9.5 (S=O)$\mu$m; NMR$\delta_{DMSOd_6}^{TMS}$ 0.90, 1.12 (two 3H singlets, $CH_3$), 4.4–5.0 (m, 2H, C=$CH_2$); 5.2–5.35 (m, 2H, O—CH—O)ppm; Anal. Calc. for $C_{33}H_{55}O_{16}S \cdot H_2O$:C, 51.20; H, 7.00; S, 3.91; Found: C, 51.23; H, 7.03; S, 4.08.

C. Stability Test

Steviolbioside, 3-sulfopropyl ester, potassium salt prepared in Part B. was incubated anaerobically for three days at 37° C. with 5 wt% fresh rat cecal contents, at concentrations of 0.25, 0.5, and 1.0 mg/ml in sterile Krebs-Ringer 0.25M phosphate buffer (pH 7.4) containing 0.25 mg/ml dithiothreitol and 0.25 mg/ml $\alpha$-D-glucose. TLC [silica gel F-254; $CHCl_3$:$CH_3OH$:$H_2O$ (15:10:2)] and HPLC [30 cm C-18 on $\mu$-Bondapak; 15 min linear gradient of 10–40% $CH_3CN$ in 0.005M $KH_2PO_4$ (pH 3.45); 200 nm] analysis showed all the initial ester (Rf=0.42; $t_R$=14.0 min) to have been consumed within 24 h to yield apparently only the sulfopropyl ester of steviol, ($R_f$=0.63; $t_R$=16.3 min). No steviol ($R_f$=0.95; $t_R$=31.3 min) was detected. After 3 days the bacterial cells were sedimented by centrifugation. The sediment was extracted (THF), as was the supernatant, after lyophilization. HPLC analysis for steviol of the two THF extracts showed none to be detectable. With a detection limit of 0.05 g, as little as 0.03 and 0.13 percent degradation to steviol could have been detected for the sediment and supernatant fractions, respectively.

As has been shown above, the sulfopropyl ester moiety is quite stable to the biological conditions which readily degrade the glycosyl ester of stevioside.

D. Taste Test

Steviolbioside, 3-sulfopropyl ester, potassium salt prepared in Part B. was dissolved in distilled water at a concentration of 0.2 wt% and tasted by a group of volunteers. The solution had a very intense sweet taste. The solution was diluted to 0.0534 wt% and retasted. It had a sweetness equivalent to 8–9 wt% sucrose, dependent on the taste tester. The taste was very sucrose-like, having negligible off-flavors. The more detailed results of this tasting are given in Table II where the taste of the test compound is shown to be superior to the tastes of saccharin and stevioside itself.

desired compound which was then recrystallized (MeOH) to yield a crystalline solid with 1½ waters of hydration.

C. When tested, this material was observed to be sweet, like the material of Example I.

EXAMPLE IV

Preparation of a compound wherein
$R = -CH_2-CH_2-NH_3^+Cl^-$

TABLE II

Sensory Comparisons of Stevioside, Analogue and Saccharin.

| Compound | Judgements | Conc. ppm | $I_p{}^a$ | $P_w{}^b$ | $P_M{}^b$ | Taste Character, % | | | | | Sweet/bitter, other |
|---|---|---|---|---|---|---|---|---|---|---|---|
| | | | | | | Sweet | Sour | Salty | Bitter | Other | |
| Stevioside | 12 | 500 | 0.94(0.06) | 190(10) | 440(30) | 62(10) | 0(0) | 0(0) | 30(10) | 8(5) | 62/38 |
| Compound of Example 1 | 12 | 534 | 0.84(0.06) | 160(10) | 360(20) | 92(6) | 0(0) | 0(0) | 4(6) | 4(4) | 92/8 |
| Saccharin | 12 | 330 | 0.98(0.09) | 300(30) | 180(20) | 85(6) | 0(0) | 0(0) | 12(8) | 3(2) | 85/15 |

$^a$Sample intensity relative to 10% sucrose; data are reported as follows: mean value(2 Sm). Standard deviation from the mean.
$^b P_w$ = compound potency compared to sucrose = 1 calculated on a weight basis; $P_m$ = compound potency compared to sucrose = 1 calculated on a molar basis.

E. Use in Comestibles

Based on the results of Part D, one can employ the compound of Part B as a sweetener for comestibles. In exemplary uses 0.08% by weight of the compound is dissolved in an unsweetened cola beverage, a like concentration of the compound is added to an unsweetened lemonade and to coffee. In each case, sweetness is imparted. In two other cases, 0.04% by weight is added to coffee along with 0.02% by weight of saccharin and 3% by weight of sucrose, respectively. Again, sweetness is imparted by the compound of Part B.

EXAMPLE II

The preparation of Parts A and B of Example I is repeated with one change. In Part B, in place of potassium carbonate, sodium carbonate is employed. This forms steviolbioside, 3-sulfopropyl ester, sodium salt. The identical product could be achieved using an ion exchange resin to replace K+ with Na+, similarly ½Ca++ or ½Mg++ could replace K+. When this material is evaluated, as in Parts C, D and E of Example I, it exhibits the same advantageous properties observed with the material of Example I.

EXAMPLE III

Preparation of steviolbioside, 4-sulfobutyl ester, sodium salt

A. Part A of Example I was repeated on a multigram scale to generate a stock of steviolbioside.

B. Steviolbioside (2 mmol) was placed in a 50 ml round bottom flask. DMF (30 ml) was added as was 2.2 mmol of NaH. This mixture was slurried under argon until foaming ceased. Then 2.2 mmole of 1,4-butane sultone was added. The mixture was stirred at 32° C. for several days, periodically checking for reaction completeness by TLC and periodically adding an additional 1.1 mmol of NaH and 2.2 mmol of 1,4-butane sultone. A product formed and was worked upon by (a) NaOH addition to hydrolyze excess 1,4-butane sultone, (b) dilution to 100 ml with water, (c) titration to pH 6 with H₂SO₄, (d) evaporation to dryness, (e) extraction with methanol, recovering and evaporating the extract to give a viscous oil (f) purification of the oil (in methanol) by preparative radical chromatography using chloroform:methanol:water (80:19:2), and (60:40:2) as eluent. Fractions were assayed and evaporated to yield the Steviolbioside (1 mmole) and K₂CO₃ (2 mmol) were added with 10 ml of distilled DMF to a 25 ml flask under argon. 1,2-dibromoethane (10 mmol) was then added and the mixture stirred at 40° C. overnight. The next morning the reaction was judged complete by TLC assay to yield steviolbioside 2-bromoethyl ester. This material was mixed with 40 mmol of NaN₂ and stirred overnight at about 25° C. to convert to the 2-azidoethyl ester. This reaction product was added to 50 ml of 1% HCl at which point a white ppct. formed and was recovered by filtration, and dried. This dry product (0.2 mmol) was dissolved in 10 ml CH₃OH, 10 ml THF and 1.5 ml CHCl₃ and mixed with 13 mg of 5% Pd on BaSO₄. Hydrogen was bubbled through the reaction at 5° C. overnight. Later the reaction mixture was warmed to room temperature and an additional 13 mg of catalyst was added. When TLC checks showed no further reaction, the solution was filtered through a millipore filter, evaporated to dryness, dissolved in water, filtered and evaporated to dryness to give steviolbioside, 2-aminoethyl ester, hydrochloride.

EXAMPLE V

Preparation of compound wherein R equals
—CH(COOH) CH₂—CH₂—COOH

Steviolbioside (5 mmol) was dissolved in 20 ml of dry DMF under argon. K₂CO₃ (6.2 mmol) was added with 20 ml DMF. and 6.2 mmol of Br—CH(COOH₃)—CH₂—CH₂—COOCH₃. The mixture was left to stir at room temperature for several days. When examined, reaction was found complete. The mixture was worked up by ice water addition, HCl addition (to pH 6.5) solvent evaporation, followed by column chromatography using CHCl₃—MeOH as eluent. A product wherein R=—CH(COOCH₃)—CH₂—CH₂—COOCH₃ was recovered off the column in 81% yield. This product was hydrolyzed by adding 50 ml of methanol and 50 ml of 10% KOH and stirred at room temperature for 30 minutes to effect conversion to the desired diacid salt. This product was neutralized with HCl, filtered and, recrystallized from acetone:methanol 100:1. This yielded the desired diacid.

This material is sweet and can be used to sweeten comestibles.

EXAMPLE VI

Preparation of compound wherein R equals
CH₂—CH₂—CH(NH₃+)—COO⁻

The "R-addition agent",

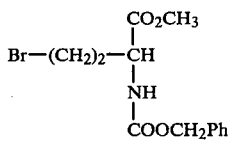

was obtained as shown in Example I of DuBois et al U.S. Pat. No. 4,226,804 which is incorporated by reference.

Steviolbioside (2.0 mmol), $K_2CO_3$ (2.5 mmol) and R addition agent (2.5 mmol) were placed in a flask with 25 ml of dry DMF uner argon and stirred at room temperature overnight. The addition reaction appeared complete by TLC. The product was extracted with ethylacetate. The extracts were washed, dryed and evaporated to yield a solid product.

The solid product was then dissolved in 30 ml of methanol and 30 ml of 10% NaOH and heated to reflux. It was refluxed until no starting material was left by HPLC. The methanol was then evaporated and the remaining product titrated to pH 6.0 with 2N $H_2SO_4$, and then evaporated to dryness. The solid was extracted with boiling methanol and the extracts concentrated to yield the desired solid product.

This material was "taste tested" and found to be sweet and sucrose like.

EXAMPLE VII

Preparation of Steviolbioside ester where R is
CH₂—COONa

A. Steviolbioside (1.29 g 2.0 mmol), $K_2CO_3$ (2.5 mmol) and 20 ml of dry DMF were placed in a flask under argon and mixed into solution. Ethyl chloroacetate (2.5 mmol) was added and the mixture was stirred at 43° C. for five hours. The reaction appeared complete by TLC so it was cooled and worked up by addition to excess chilled 5% HCl whereupon a precipitate formed that was recovered by filtration. This product had as its C-19 oxygen substituent, —CH₂—CO₂—C₂H₅.

B. The ethyl protecting group was hydrolyzed by treatment with 10% KOH until TLC assay showed reaction completion. The product was precipitated on acidification (10% HCl) to pH 3 and was isolated by filtration. The product was dissolved in 1.00 equivalent 1.00M NaOH and the resultant solution lyophilized. Recrystallization (MeOH) yielded the desired steviolbioside, carboxymethyl ester, sodium salt. This compound shows m.p. 230°–240°(dec)

Elemental Analysis Calculated for $C_{34}H_{51}O_{15}Na.1 H_2O$: C 55.12, H 7.21. Found: C 55.06, H 7.14.

C. This material was sweet when tasted by a group of volunteers.

EXAMPLE VIII

Preparation of Compound where R equals
—CH₂—CH₂—CH(SO₃⁻)₂Na₂⁺

A. Propane sultone (1.00 mmol) and 2.0 ml of dry THF were placed in a round bottomed flask. n-butyl lithium (1.10 m mol of 2.4M solution) was then added dropwise over five minutes while stirring vigorously under argon and cooling at −78° C. The mixture was stirred for about five minutes and 1.10 mmol of

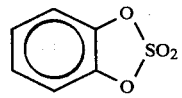

was added along with 2.0 ml of THF, and this mixture was stirred at −78° C. for 30 minutes.

The product was worked up by being added to 20 ml of ice/10% HCl; saturated with NaCl, and extracted twice with diethyl ether. The extracts were dried and concentrated to yield the crude product as an oil. This oil was purified by passage through a silica gel plug, washing with CHCl₂—MeOH and rotary plate thin layer chromatography. The identity of the desired product

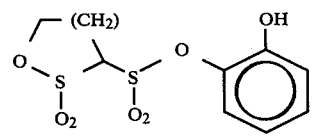

was confirmed by IR and NMR analysis.

B. Steviolbioside (1.72 g 2.68 mmol) was dissolved in 20 ml of dry DMF. 5.2 ml of 0.5M Potassium-amyloxide toluene solution (2.68 mmol) was then added. The R-addition agent of Part A (2.68 mmol) was added and stirred at room temperature for 72 hours. The reaction mixture was evaporated to yield an oily residue which was dissolved in 25 ml of water and brought to pH 6 with HCl. This gave an amber solid upon evaporation which was dissolved in methanol and purified by rotary silica gel chromatography. The desired product was isolated and recrystallized from methanol/water to give a white crystalline solid.

C. The solid (878 mg 0.90 mmol) of part B was dissolved in 88 ml of distilled water under argon. 0.99 mmol of 0.11M KOH was then added and the mixture refluxed for 4½ hours. An additional 0.5 mmol of KOH was added and reflux continued for 2¼ additional hours. The reaction was cooled, neutralized and concentrated to dryness to yield an amber solid. This product was then dissolved in water, purified by rotary silica gel chromatography, converted to the sodium salt by ion exchange chromatography and recrystallized (EtOH—H₂O) to produce 370 mg of off white granular crystals of the steviolbioside ester compound wherein R is —CH₂—CH₂—CH(SO₃⁻)₂Na₂⁺.

D. The compound of part C was dissolved in distilled water at a concentration of 1000 ppm by weight. It was exceedingly sweet, at least equal in intensity to a 10–12% sucrose solution.

EXAMPLE IX

It will be appreciated that the sweeteners of the invention can be incorporated into a wide range of comestibles.

Cups of coffee are prepared: To each is added 500 ppm by weight, basis solution, of one of each of the sweeteners prepared in Examples II–VIII. The coffees present a sweetened taste when sampled.

Gelatin, food color and fruit flavor are dissolved in water at levels suitable for forming a jelled food product. The solution is not sweet. The materials of Claims II–VIII are each added to separate samples in amounts of 600 ppm and the samples are cast into jelled products. The resulting gelatin products are sweet.

What is claimed is:

1. A steviol analogue compound having the structure

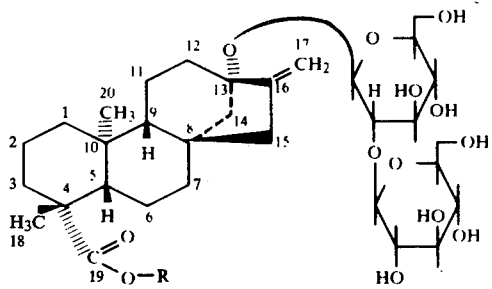

where R is a member selected from the group consisting of 1–5 carbon alkyl terminal sulfonates, alkyl polysulfonates of the formulae $-CH_2-CH-(SO_3^-M^+)_2$, $-(CH_2)_2-CH-(SO_3^-M^+)_2$, and $-CH_2-CH-(SO_3^-M^+)-CH_2-CH_2-SO_3^-M^+$, 1–5 carbon alkyl terminal carboxylates, an alkyl polycarboxylate of the formula $-CH_2-COO^-M^+-(CH_2)_2-COO^-M^+$, 1–5 carbon alkyl terminal phosphonates, polyhydroxyl alkyls of the formulae $-(CH_2)_n-CH(OH)-CH(OH)-CH_2OH$ and $-(CH_2)_n-CH(OH)-CH_2OH$ wherein n is 1 or 2, 1–5 carbon alkyl primary amine salts of the formulae $-(CH_2)_n-NH_3^+N^-$ wherein n is an integer from 1 to 5 inclusive, 1–5 carbon alkyl sulfonates and 1–5 carbon alkyl amino-carboxylates wherein $M^+$ is a physiologically acceptable alkali metal or alkaline earth metal cation and $X^-$ is a physiologically acceptable anion.

2. The compound of claim 1 wherein R is a 1 to 5 carbon alkyl terminal sulfonate.

3. The compound of claim 2 wherein R is of the formula $-(CH_2)_n-SO_3^-M^+$ wherein n is an integer from 2 to 5 and $M^+$ is a physiologically acceptable alkaline earth metal cation or alkali metal cation.

4. The compound of claim 3 wherein n is 3 or 4 and $M^+$ is selected from $Na^+$, $K^+$, $\frac{1}{2}Ca^{++}$ and $\frac{1}{2}Mg^{++}$.

5. The compound of claim 4 wherein n is 3 and $M^+$ is $Na^+$ or $K^+$.

6. The compound of claim 1 wherein R has a formula selected from $-(CH_2)-CH-(SO_3^-M^+)$ and $-(CH_2)_2-CH-(SO_3^-M^+)_2$ and $M^+$ is a physiologically acceptable alkaline earth metal cation or alkali metal cation.

7. The compound of claim 1 wherein R is of the formula $-(CH_2)_n-COO^-M^+$ wherein n is an integer from 1 to 5 inclusive and $M^+$ is a physiologically acceptable alkaline earth metal cation or alkali metal cation.

8. The compound of claim 1 wherein R is an alkyl terminal phosphonate of the formula $-(CH_2)_n-PO_3H^-M^+$ and n is an integer from 1 through 5 inclusive and $M^+$ is a physiologically acceptable alkaline earth metal cation or alkali metal cation.

9. The compound of claim 1 wherein R is an alkyl polycarboxylate.

10. The compound of claim 1 wherein R is a polyhydroxyl alkyl.

11. The compound of claim 1 wherein R is a primary alkyl amine salt.

12. The compound of claim 1 wherein R is an alkyl sulfonate.

13. The compound of claim 1 wherein R is a 2 to 5 carbon alkyl amino carboxylate.

* * * * *